United States Patent [19]

Saxholm

[11] 4,213,825
[45] * Jul. 22, 1980

[54] APPARATUS FOR TESTING REACTIONS

[76] Inventor: Rolf Saxholm, Box 3, 1362 Billingstad, Norway

[*] Notice: The portion of the term of this patent subsequent to May 3, 1994, has been disclaimed.

[21] Appl. No.: 716,684

[22] Filed: Aug. 23, 1976

Related U.S. Application Data

[63] Continuation-in-part of Ser. No. 502,107, Aug. 30, 1974, Pat. No. 3,981,776, which is a continuation-in-part of Ser. No. 156,738, Jun. 25, 1971, Pat. No. 3,843,450, which is a continuation-in-part of Ser. No. 705,539, Feb. 14, 1968, abandoned.

[51] Int. Cl.$^2$ ............................................... C12K 1/00
[52] U.S. Cl. ...................................... 435/291; 422/57
[58] Field of Search .............. 195/127, 139; 23/253 R

[56] References Cited

U.S. PATENT DOCUMENTS

| | | | |
|---|---|---|---|
| 2,971,892 | 2/1961 | Carski | 195/139 |
| 3,474,004 | 10/1969 | Fink | 195/139 |
| 3,540,985 | 11/1970 | Gross | 195/127 |
| 3,684,660 | 8/1972 | Kereluk et al. | 195/139 |
| 3,776,818 | 12/1973 | Khan | 195/139 |
| 3,799,844 | 3/1974 | Campbell et al. | 195/127 |
| 3,837,745 | 9/1974 | Acker et al. | 195/127 |
| 3,899,011 | 8/1975 | Curtiss | 195/127 |
| 4,021,308 | 5/1977 | Saxholm | 195/127 |

OTHER PUBLICATIONS

Analytical Microbiology, F. Kavanagh pp. 118, 119, 219-223, 268, 269, 276, 335-337 and 402-404 (1963).
Automation in Turbidimetric Assays, Hucke et al. from Antibiotics Annual (1959-1960) pp. 556-562.
Instruments vol. 22 p. 54 (1949).
Fisher Scientific Co. p. 296 (1967).

Primary Examiner—Alvin E. Tanenholtz
Attorney, Agent, or Firm—Haseltine, Lake & Waters

[57] ABSTRACT

A biologically active substance is incorporated in a unitary body with a magnetically responsive material for carrying out diffusion testing. These may be, microbiological, immunological, serological and other biochemical examinations. The body is applied against a substrate or medium by application of an external magnetic field and a reaction region is produced at the site of the body and is measured by means of a reader. In order to insure deposit of the body on the substrate a predetermined location and corresponding reading of the reaction region at such location, the support for the substrate and the dispenser and reader are provided with suitable releasable coupling and orienting devices such that the dispenser and reader can be respectively engaged and oriented on the support in predetermined secured positions.

12 Claims, 16 Drawing Figures

APPARATUS FOR TESTING REACTIONS

This application is a continuation in part of application Ser. No. 502,107 filed Aug. 30, 1974 issued as U.S. Pat. No. 3,981,776 which in turn is a continuation-in-part of Ser. No. 156,738 filed June 25, 1971 issued as U.S. Pat. No. 3,843,450 which in turn is a continuation-in-part of application Ser. No. 705,539 filed Feb. 14, 1968 and now abandoned.

BACKGROUND OF THE INVENTION (a) Field of the Invention

The invention relates to diffusion testing in which the result is indicated by a change in growth and/or other reaction. Such testing includes tests which may be biological (i.e. microbiological, immunological, serological and other biochemical tests inclusive of clinical chemical tests) or chemical as long as they are suitable for diffusion testing.

(b) Description of the Prior Art

Microbiological and immunological tests are often carried out by depositing an article for testing sensitivity, usually in the form of paper discs, tablets, or similar bodies, containing biologically active substances upon the surface of a solid or semi-solid substrate or medium. In the case of microbiological testing, the biologically active substance reacts with a culture of microorganism inoculated on or in the substrate or with various substances in the substrate produced by the microorganism, whereas for immunological testing the active substance reacts with various substances, e.g. a serum added to the substrate or with various substances produced by a microorganism.

The substances deposited are diffused downwardly into the solid or semi-solid substrate to react with the aforementioned agents in the substrate, i.e., the microorganism or substance produced by the microorganism in the case of microbiological testing, and the added substance or substance produced by a microorganism in the case of immunological testing.

A common test of this type is the determination of sensitivity of microorganisms, e.g. bacteria, to biologically active substances, e.g. antibiotics, chemotherapuetics, etc. These experiments are frequently carried out by inoculating the substrate with the bacterial culture to be determined. Then the biologically active substance, i.e. an antibiotic contained in an article in the form of a paper disc or tablet, is deposited on the substrate, either manually or mechanically, and then pressed lightly into contact with the substrate with a sterile needle, tweezers or the like. The disc or tablet is absorbent and the solid and semi-solid substrate contains aqueous medium which is absorbed in the disc or tablet whereupon the antibiotic is dissolved and diffuses into the substrate. The substrate is then placed in an incubator and, after sufficient time, the effect of the antibiotic is noted by measuring the diameter of the circular zone of inhibition of the growth (i.e. region of sensitivity) surrounding the article. Mention should also be made of the use of biologically active substances which stimulate or enhance growth, i.e. of growth factors and growth requirements, such as vitamins, amino acids, peptides, proteins, carbohydrates and minerals.

Various other examinations which involve diffusion and change in growth and/or other reaction in a solid or semi-solid substrate e.g. radial immunodiffusion, can also be performed by the above method. Additionally, since diffusable agents from the substrate contained in the aqueous medium will diffuse into the article, it is also possible to perform examinations which involve reaction in the article.

In order to compare the test results of bacterial sensitivity to various antibiotics, or the other biologically active substances, it is essential that uniform and good contact between the article containing the biologically active substance and the substrate is obtained. It is also important to achieve as uniformly adjusted contact as possible from one sensitivity test to the next in order to compare the results and establish a basis for reliability.

A frequent source of error in determining sensitivity occurs when the article containing the biologically active substance is deposited or placed askew on the substrate. Because of incomplete contact between the article containing biologically active substance and the substrate, diffusion into the substrate will be impaired since the amount of diffusion is a function of the contact area. Good contact results when the intended contact surfaces are in substantially complete and uniform contact thus resulting in suitable and reproducible amounts of diffusion.

If uniformly good contact between the article containing the biologically active substance and the substrate containing the microorganism is not achieved, diffusion of the biologically active substance into the substrate will not be uniform and consequently a standard diffusion test procedure cannot be developed, since diffusion is highly dependent on the size of the contact area. The results of sensitivity tests determine to a large extent how patients with infections diseases shall be treated.

Heretofore, it was impossible manually to achieve a uniformly good contact between biologically active substance and the bacteria-containing substrate or medium from one sensitive test to the next. Since laboratory technicians vary in manual dexterity, proficiency, and work experience, it is not surprising that uniformly good contact cannot be achieved from one sensitivity test to another. Even greater variations in results can be expected between different laboratory technicians.

Although many attempts were made to overcome the foregoing and other difficulties none, as far as I am aware, was entirely successful when carried into practice commercially on an industrial scale.

SUMMARY OF THE INVENTION

An object of the invention is to provide an article containing an active constituent suitable for testing various reaction i.e. changes in growth and/or other reactions with an agent in a substrate by diffusion of the active constituent in the article into said substrate, or by diffusion of the agent contained in the substrate into the article.

Another object of the invention is to provide a method and apparatus for testing reactions using the above articles and substrates.

A further object of the invention is to make the method and apparatus operative automatically under the control of an operator.

According to the invention, a magnetically responsive means is incorporated with the active constituent to form a unitary body which can be brought into contact with the substrate by application of an external magnetic force.

The active constituent may be an antibiotic for microbiological sensitivity testing, or for immunological testing it may be an antigen for testing antibodies in the substrate or vice versa.

In general, the active constituent reacts with the age of the substrate, either by diffusing into the substrate or by diffusing of the agent into the article containing the active constituent or by the combination thereof.

The article comprises a wettable or absorbent carrier which carries the active constituent and is inert thereto, said carrier being substantially insoluble in the substrate.

In further accordance with the invention, the apparatus for testing reactions comprises a support for a substrate, dispenser means for depositing a plurality of articles containing respective active constituents onto said substrate in spaced relation, said constituents undergoing varying, i.e. different reaction with an agent in said substrate and producing detectable results, index means for orienting the dispenser means and said support relative to one another to predetermine the locations of said articles on the substrate, and reader means correlated with said index means for determining said detectable results at said predetermined locations.

It is further contemplated according to the invention that the articles may in some instances contain no active substance prior to use but incorporate only the magnetically responsive material. The articles are initially porous and dry i.e. they are formed, for example, as paper discs and the active substance or test materials are added to the discs either before or after they are deposited on the substrate. Preferably the active substance or test materials are in liquid form although it is also feasible to utilize them in solid form such as powders.

DETAILED DESCRIPTION

Figure 1:
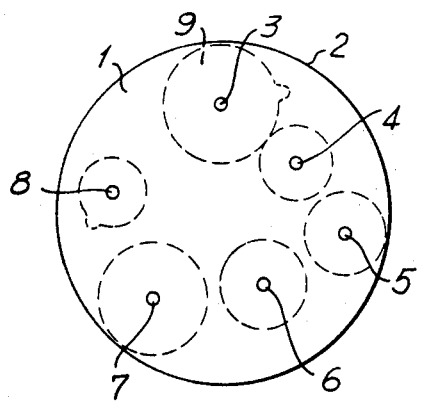
FIG. 1 is a plan view showing tablets containing biologically active substances placed at random on a substrate with varying zones of inhibition.

In carrying out this invention, a petri dish or other receptacle containing a solid or semi-solid substrate with a culture of a bacterium or other microorganisms is associated with a means for establishing a magnetic field such as, for example, one or more permanent or electromagnets attached to the bottom of the dish or incorporated in a supporting base for the petri dish. Thereafter an article containing a biologically active substance and a magnetically responsive material is placed on the substrate and, through the action of magnetic force, forms a uniformly good contact with the substrate, thus avoiding the use of manual or mechanical pressure on the article to establish contact. The petri dish is placed in an incubator and the biologically active substance in contact with the substrate is then allowed a sufficient period in the incubator to produce growth and/or other reaction. Thereafter, a region or zone in which the biologically active substance has inhibited, stimulated, or produced no change in bacteria growth is visible to the eye. The measurement of this zone or region of sensitivity results in an accurate measurement of the sensitivity of the microorganism being tested to the particular biologically active substance.

The method of accurately measuring the sensitivity of a microorganism to a biologically active substance involves the steps of forming a substrate containing a microorganism; placing an article containing a biologically active substance having incorporated therewith a magnetically responsive material on the substrate (or on a predetermined position of the substrate); causing a magnetic force to act on the article whereby the article is urged against the substrate and forms good contact therewith; allowing sufficient time for the biologically active substance to act on the microorganism; and thereafter measuring the sensitivity region surrounding the article. The magnetic field need not be applied until the article is deposited, although I prefer to have the magnetic force acting on the article at the time of its release and prior to initial contact with the substrate so that the article will be deposited in proper position on the substrate. After good contact between the article and the substrate is achieved, the magnetic force may be removed.

The articles may initially be blank and incorporated only the magnetically responsive material, and solutions of active substance can be added to the articles either before or after the articles have been positioned on the substrate. This will be explained in greater detail later.

This invention also provides an apparatus for testing the sensitivity of a microorganism in which a receptacle suitable for holding a solid substrate (such, for example, as a petri dish) is provided with means for applying magnetic field to the substrate so that when an article which comprises a biologically active substance having incorporated therewith a magnetically responsive material, is placed on the substrate, the article is urged against the substrate and establishes good contact therewith to permit accurate measurements of the sensitivity of the microorganism to the biologically active substance.

In addition, a mechanical dispensing means can be used for dispensing the magnetically responsive articles with biologically active substance in random or predetermined positions on the substrate, the dispensing means being provided with a plurality of dispensing columns or tubular members. Also provided is an index means to provide orientation between the dispensing means and the receptacle to enable the articles with the biologically active substances to be deposited on the substrate in predetermined position. Such index means could, for instance, consist of register marks on the receptacle or its support base at predetermined distances which correspond to similar marks on the dispensing apparatus at corresponding distances. The index means could also consist of a detent or locking means.

In conducting the sensitivity measurements, various mechanical reader means are provided to facilitate actual measurements of the sensitivity regions surrounding the articles containing the biologically active substances. For example, an instrument provided with adjustable apertures arranged in a predetermined pattern corresponding to the deposition points of the article on the substrate can be brought into alignment therewith by cooperation with the index means, and the respective apertures adjusted to cover the sensitivity areas or respectively adjusted to grade different degrees of positive reactions or no reaction. The grading may be indicated by means of special switches or buttons. A mirror reflex instrument is also a satisfactory means for determining sensitivity. The general method of measuring sensitivity involves the measurements of the diameter of the sensitivity region which is normally circular and surrounds the article containing the biologically active substance.

Although the invention will be discussed chiefly in relation to the sensitivity of a microorganism to an antibiotic and vice versa, the invention is broadly concerned with the use of articles associated with active substances whose reactivity with an agent in a substrate is detectable. Thus, for example, in immunological testing, the articles contain an antigen to detect the presence in the substrate of an antibody or vice versa. Also, for example, it may be used for radio-immunodiffusion techniques and for fluorescent immuno-diffusion techniques. In general, any detectable reaction which occurs by means of diffusion of the active substances in the article into the substrate or of the agent in the substrate into the article is applicable to the present invention. The reaction may be detectable by the eye, by a spectrophotometer or by a radiation detector. The detectable change which may take place within the article itself, may for example, be a test for urease production by microorganisms by color change in the article.

As to the type of physical connection existing between an agent and a substate, various expressions have been used herein to indicate this connection. In this respect expressions have been used to refer to the agent being "in" the substrate, and correspondingly "on", "off", "contained in", "added to" and "associated with" the substrate. In respect of the invention, the essential point, whatever expression has been used, is a physical association between the agent and the substrate. It will be understood that the various terms employed, broadly should be interpreted to express this fact.

In order for diffusion to be achieved, the article must be wettable or absorbent to allow aqueous medium of the solid or semi-solid substrate to contact the active substances to provide for diffusion.

In the case of a carrier, such as a disc or a tablet for the active substance, the carrier should be substantially insoluble in the substrate to prevent any undesired influence on the diffusion process and the delicate reaction mechanism taking place, for example, by occurrence of unspecific reaction. The wettability of the carrier is achieved by rendering it microporous in which case wetting is effected by capillarity. In the case of paper discs, they for example, may be absorbent to the extent that they absorb approximately three times their weight in distilled water. The active substance should desirably be substantially uniformly distributed in the paper, and the paper should have no interfering effect on the reaction. In the case of an antibiotic, the paper should have no interfering effect either on bacterial growth or on the action of the antibiotic. As an alternative to conventional cellulose paper, various plastics satisfying the above conditions may be used as the inert carrier. Also suitable are glass fibre papers.

A dye may be incorporated in the article as coding means to indicate the particular article to identify the reaction. The dye should be substantially insoluble in aqueous medium and be inert to the reaction e.g. have no interference with the antibiotic or the growth of the microorganisms.

The articles may be supplied in a stack in a vacuum package.

Although the substrate might be a liquid, it preferably is a solid or semi-solid which is microporous and possesses a high water content in order to permit the diffusion mechanism to take place. The substrate may initially be dry and the water added thereto either directly or through the article itself. The substrate may be a gel such as a starch, gelatin, silica etc., or it may be a paper made on cellulose basis or a glass fibre paper. The most common gel is an agar gel which possesses substantial strength even with very high water content. Agar is very inert chemically and is suitable for examining diffusion tests. In case of microbiological testing the substrate will contain a nutrient and it must be sterile prior to inoculation. The substrate is placed on a support which in the case of microbiological testing is generally a petri dish or large plate whereas in the case of immunological testing it may be a coated plate. Generally the substrate has a substantially uniform composition throughout its entire extent and is constituted of one ore more prescribed components in definite amount.

Referring now to the drawings, FIG. 1 depicts articles in the form of tablets containing various antibiotics placed at random on the surface of the substrate 1 in a petri dish 2 and surrounding the individual tablets 3 to 8 are sensitivity areas 9 shown with broken lines.

FIG. 2 shows six different antibiotic tablets 10 to 15 arranged in a predetermined pattern characterized by mutual equiangular distances and radii R from the center of the petri dish 16.

FIG. 3 shows an apparatus for utilizing this invention in which a base 17 is made of a permanent magnet and on the base there is placed a petri dish 18 containing a substrate 19 and six different antibiotic tablets 10 to 15 placed thereon corresponding to those shown in FIG. 2. These tablets are placed in predetermined positions by a dispensing apparatus 20 which consists of six tubular members 21 to 26, preferably constructed from nonmagnetic material, which at their lower ends are connected to a housing 27 and at their upper ends are connected to a supporting plate 28. Each of the tubular members contains a stack of articles, the articles originally having been supplied in a vacuum package. In the housing 27, there are on each of the tubular members, depositing mechanisms of known construction which are familiar to those skilled in the art for releasing articles one at a time from each tube in one operation. The supporting plate 28 is suspended from an arm 29 which in turn is adjustably suspended in a manner known to those skilled in the art in such a way that the dispensing apparatus 20 may be moved up and down and can be swung from side to side in order to facilitate a correct positioning of the dispensing apparatus 20 relative to the dish 18. The dispensing apparatus can be brought into correct position relative to the petri dish with the register marks 30 and 31 on the petri dish and base corresponding to the register marks 32 and 33 on the housing 27. It is also possible to fix the dispensing apparatus and make the petri dish movable. It is further possible to lock the petri dish on the base and make either the dispensing apparatus or the assembly of base and petri dish movable. Instead of register marks, detents or other releasable locking means can be employed.

Figure 4:
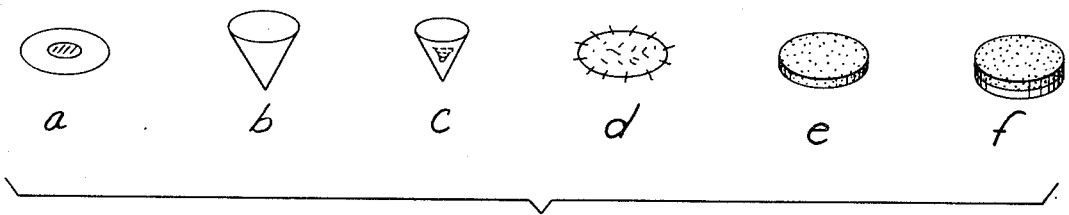
FIG. 4 shows several embodiments of carriers with active substances of various shapes and incorporating magnetically responsive material.

FIG. 4 depicts several embodiments of the article for testing sensitivity in accordance with this invention and which may be provided, for example, with a heavy magnetically resposive core as shown in FIG. 4a. The core can be press fit into the article. Alternatively, the magnetically responsive material could be in the form of an annulus around the article. FIGS. 4b and 4c depict the article in the form of a conical projectile to enable good contact with the substrate. FIG. 4d shows the tablet with anchoring devices which, for example, can be a magnetically responsive material such as iron, and which prevent the tablet from recoiling when deposited on the substrate. The paper discs and tablets may be impregnated or admixed with a magnetically responsive material as shown in FIG. 4e or the paper discs or tablets may be provided with magnetically responsive components such as a foil attached by adhesion as shown in FIG. 4f. In lieu of particles, the magnetically responsive material could be in the form of a grid or foil embedded in the article. In order to prevent any interference of the magnetically responsive material with the reactants, an inert envelope may be applied to the magnetically responsive material. In the case of the embodiment shown in FIG. 4a, the entire core is covered with a single inert envelope, whereas in the embodiment in FIG. 4c, the individual magnetically responsive particles may be coated prior to incorporation in the carrier.

Figure 2:
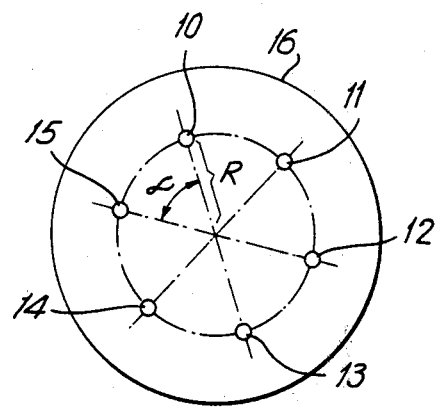
FIG. 2 is a plan view showing six different biologically active substances in respective carriers arranged in a predetermined pattern on a substrate.
Figure 5:
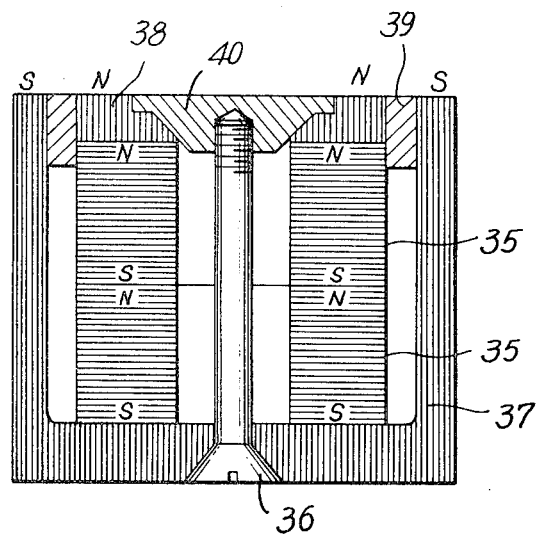
FIG. 5 is a vertical section of one embodiment of a magnet system.

FIG. 5 illustrates schematically a simple embodiment of magnet system which can be used in the base of the apparatus when the deposition points on the substrate are disposed in a circle as in FIG. 2. A permanent magnet comprised of two axially magnetized Ticonal ring magnets 35, one on top of the other, is affixed by means of an aluminum bolt 36 to a soft iron cup 37 which, together with a circular pole piece 38 on the top of the magnet rings, encircles a circular air gap facing upwards, which, like the central bore of the magnet, is filled with non-magnetic material, e.g. aluminum, as shown at spacers 39 and 40, to give the base a smooth upper surface. The air gap has a mean diameter equal to the diameter of the circle of positions (FIG. 2), which in turn is determined by the positions of the outlets of the dispenser, and the width of the air gap has to be adjusted to the height to the surface of the substrate, so that a substantial field component is able to act on the articles on the substrate. With the substrates generally used, this height will normally be approximately 4–5 mm, and the width of the air gap should in that case be about the same.

Figure 3:
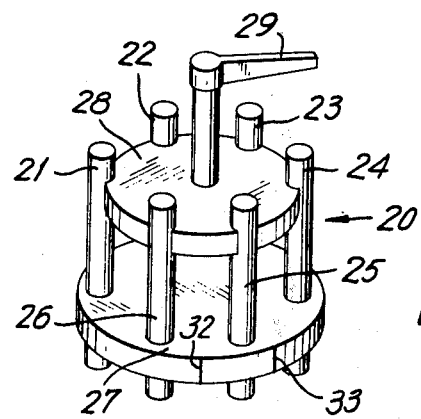
FIG. 3 diagrammatically shows in perspective an apparatus for dispensing articles containing active substances on a substrate in a petri dish provided with a permanent magnet.
Figure 3:
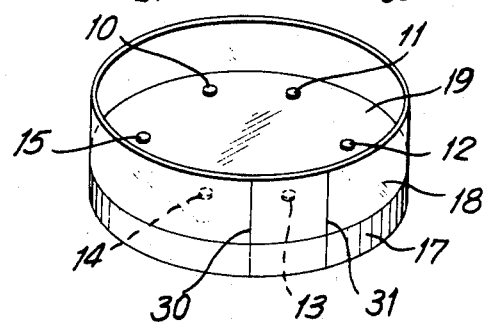

Laboratory tests employing six different active substances as illustrated in FIG. 2, and with a device as shown in FIGS. 3 and 5 have been used and by way of example mention may be made of studies of the inhibiting effect of antibiotics in resistance determination, where, on an inoculated substrate consisting of, for example, a blood agar without a peptone additive, are deposited paper discs containing such active substances as, for example:

Penicillin, sulphonamide, tetracyclin, erythromycin, methicillin, fucidin, streptomycin, nitrofurantoin, ampicillin, and nalidixin.

Articles can be used for other purposes than antibiotic sensitivity testing, as previously mentioned, and by way of example the active substance in the article may be an antigen or an antibody for immunological testing of an agent added to the substrate. Furthermore, the testing need not be biochemical, but may also be purely chemical, such as, determination of pH of the substrate within narrow limits by use of articles containing respective chemical indicators undergoing changes of color at different pH values.

It may also be mentioned that a number of active substances may be supported on a common carrier. In such case, the active substances may be disposed in spaced pre-determined locations on the common carrier with the magnetically responsive material either incorporated with the active substances, as in the previously described embodiments, or maintained separate therefrom in the spaces between adjacent substances.

Figure 6:
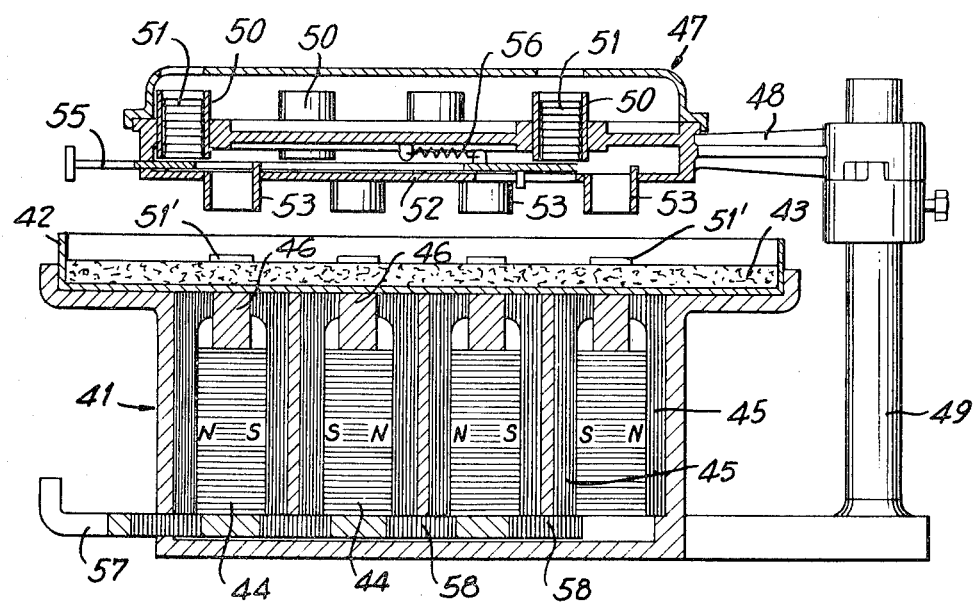
FIG. 6 is a vertical section of a dispenser with a different embodiment of a magnet system.

FIG. 6 shows in greater detail another embodiment of magnet system and a dispenser especially useful when discs in large numbers are to be deposited. An aluminum base 41 is shown for centering and supporting a dish 42 containing a substrate 43 and the base 41 contains a buitl-in system of magnets consisting of horizontally magnetized permanent magnets 44 which lie parallel to one another and are magnetized alternately each in opposite directions and each of which is flanked by a pair of pole pieces 45 lying on edge which form air gaps 46 facing upwards at the upper surface of the base. Between each pair of magnetic poles there is a completely symmetrical flux field with the plane of symmetry in the middle of the air gap.

The dispenser 47 is supported by means of an arm 48 on an upright 49 on the frame 41 for pivotal movement in a horizontal plane from the illustrated active position, which is determined by a stop, to an inactive position where the dish 42 can be inserted and removed. The apparatus contains vertical dispensing tubes 50 adapted to hold stacks of discs 51 provided with magnetically responsive material, for example, in the form of an iron foil affixed by adhesion. The stacks of discs normally rest on a baseplate 52, which is fitted with outlets 53 laterally displaced in relation to the relevant dispensing tube 50. The bottom disc in each stack is moved to the associated aperture by moving a pusher 55 against the bias of a return spring 56. In the case illustrated, the pusher 55 is provided with a stright translational guiding support which is preferred in dispensers with a plurality of magazines, as opposed to rotatable pushers, which are usually simplest when all the magazines are on a common circle.

The base 41 and the dispenser 47 can be aligned with one another such that the outlets 53 in the operating position are directly above the air gaps 46. Each set of discs released will thus fall parallel from the outlets 53 in symmetrical magnetic fields and be positioned on the substrate 43 directly above the air gaps as shown at 51', and be drawn into uniform contact with the substrate.

Should it be desired to regulate the strength of the magnetic field, this may be effected by a pusher 57, which is supported for movement across the magnets 44 at the bottom of the base 41 and the pusher is fitted with pieces of soft iron 58, which in the illustrated position lie directly beneath successive pole pieces 45, but by displacement can be caused to project more or less into the space between paired pole pieces on the underside of the respective magnets and thus more or less shunt the effective field. By being moved to a central position underneath the magnet the pieces of soft iron 58 can be made almost to short-circuit the magnetic fields, so that the effect on the upper side is annuled if it should be so desired, to guard against any magnetic action on the discs while the dish is being removed. In order to remove the dish without annulment, it is lifted from the holder 41 directly upwards a small distance, i.e. in the direction of the magnetic force so as not to disturb the position of the discs.

Among the sensitivity tests that can be undertaken with the apparatus illustrated in FIG. 5 with more than six deposition points, mention may be made solely by way of example of determination of resistance to a bacterium such as Escherichia coli of antibiotics such as penicillin, sulphonamide, streptomycin, chloramphenicol, tetracyclin, ampicillin, colistin, cephalosporin, nalidixin, nitrofurantoin, carbenicillin, and kanamycin.

The amount of magnetically responsive material in each article and the strength of the field must, of course, be adapted to each other in the light of the geometrical conditions, the orientation of the field, the permeability of the components, etc., on the basis of the contact pressure desired. For a properly adjusted contact this will be the equivalent of the light manual pressure. With ordinary disc-shaped articles of a diameter of approximately 6 mm, about 1 gram of force will generally be sufficient, and as an optional parameter 2 grams of force produces a surface pressure of about $1/10 \, g/mm^2$.

The magnet system may also comprise small cup magnets placed under the positions for the articles either in the substrate dish or, more suitably, in a base on which it stands.

To bring about the desired effect without too strong a magnetic field, the magnetically responsive material in a standard paper disc should weigh slightly more than the rest of the disc, but occupy less volume, and the amount will be only a very small fraction of what would be required to achieve the same contact pressure with the heaviness of an added weight.

Experiments with the contact pressure achieved with a system of magnets as shown in FIG. 6 have been performed with Ticonal magnets with an air gap of 5 mm, adjusted to provide a field intensity of approximately 650 Gauss at a distance of 5 mm directly above the air gap, i.e. at a height which should be quite sufficient to accommodate variations in the depth of the substrate and the thickness of the actual paper disc. The variations in field strength from block to block at this height were quite insignificant ($\pm$ approx. 25 Gauss). For a circular iron foil with a diameter of approximately 5.5 mm and weighing approximately 20 mg, the height above the air gap for magnetic forces respectively of 1 gram and 2 grams were 9.5 and 6.5 mm respectively.

The experiment was repeated with an iron foil of the same diameter and weighing approx. 12 mg (0.06–0.07 mm thick) and here the heights were 8 and 5 mm respectively.

Similar tests have also been carried out with more powerful (ceramic) parallel epipedic magnets of the Ferroxdure type, with which an air gap of 6 mm generated a field intensity of approximately 1250 Gauss at a height of 5 mm, while approximately 650 Gauss was measured at a height of 10 mm. The heights for generated forces or respectively 1 and 2 grams were in the case of the first foil 15.5 and 11 mm respectively and for the second foil 13 and 8 mm respectively. Such a system of magnets will thus be unnecessarily powerful under normal circumstances where the amounts of iron as mentioned above are used in the articles, but, may be suitable in the case of still smaller quantities of iron, or if an extra pressure is desired, e.g. on articles to be drawn into the substrate.

It is, of course, possible to replace the permanent magnets in the illustrated systems by electromagnets of similar dimensions which can be regulated or switched on and off electrically.

In the conventional manner of dispensing articles onto the substrate, the often tend to land in a somewhat oblique position on the surface. Even a slight oblique angle on landing has a disturbing effect on the possibility of providing good and uniform contact in a predetermined position with respect to the substrate.

Not only does this apply to light articles, which for inherent reasons, need an addition of a slight external pressure to establish good contact with the substrate, but also to comparatively heavy articles.

A solid or semi-solid substrate, such as an agar substrate is as a rule slippery and often somewhat elastic in its consistency. Particularly, when heavy articles are concerned, the features mentioned, will produce an undesired effect on the capability establishing adequate contact in predetermined positions with the substrate. Thus, deposition on the substrate by dropping articles from a dispenser, will, especially when heavy articles are concerned, often produce a slight, although noticeable, and disturbing rebound effect. This is due to the somewhat elastic consistency of the substrate mentioned. Furthermore, the kinetic energy of the heavy articles effected by the rebound from the substrate, especially in combination with the tendency of the articles to make a skew landing, and, with the slippery substrate, has a detrimental effect with respect to adequate positioning. The articles will more or less tend to slide out of the desired location, without establishing good and uniform contact.

The invention makes it possible to avoid the obstacles disclosed above. Thus, by means of magnetic forces it is possible, according to the invention, to deposit articles on the substrate in good and uniform contact therwith at desired predetermined positions.

Furthermore, if magnetically responsive material, for example, iron, added to an article, amounts to such a degree that the article becomes heavy, it is possible, according to the invention, to use a relatively weak magnetic field so as to create a weak magnetic force able to overcome the rebound and sliding effect produced during the initial contact between the article and substrate during deposition. A strong magnetic field may under these circumstances, using an article incorporating a relatively substantial amount of magnetically responsive material, create a magnetic force so strong that on being added to the force of pressure created by the heaviness of the article, results in an over-all pressure which may damage the supporting strength or structure of the substrate.

Articles may become heavy not only due to the added weight of the magnetically responsive material itself, but also to a combination of the magnetically responsive material, for example, iron, and other materials, for example, lead. The strength of the magnetic field to be used according to the invention, has to be adapted to the amount of iron or other magnetically responsive material present, on the basis of the initial contact pressure desired.

An askew landing of a heavy article on the substrate will seriously interact with the rebound and sliding effects, thereby seruiously disturbing the possibility of positioning the article in good and uniform contact with the substrafe in a predetermined position. According to the invention, it is possible by magnetic means to guide the article in a balanced position or equilibrium during the flight, thereby avoiding the interactions mentioned.

In this connection it should be recalled that according to the invention, it is possible by means of magnetic forces to eliminate the disturbing effects of rebound, sliding and askew landing of an article being dropped onto a substrate. As disclosed above, heavy articles are particularly liable to create rebound and sliding effects by the initial contact with a substrate.

It should be recalled that articles have been disclosed for providing good contact with deeper layers of the substrate, for example, articles in the form of conical projectiles. Such articles may also be in the form of balls. Also these articles may be made heavy by added weight, for example, by addition of a substantial amount of magnetically responsive material, for example, iron. They may also be subjected to a rebound effect from the substrate in response to the initial contact as a result of the dropping. Also in this case, it will be possible by means of magnetic forces according to the invention to eliminate the rebound and sliding effects by adapting the strength of the magnetic field to the amount of magnetically responsive material present, on the basis of the initial contact pressure desired.

The magnetically responsive material added to the article may be supported and carried by a carrier of the article.

The invention is highly suitable also for prediffusion techniques i.e. pretreated substrates which are at present used by only a few laboratories. In the method currently employed with these techniques, antibiotic bodies are placed by hand or by means of a dispenser on the substrate before inoculation is carried out. They are then lightly pressed by hand into contact with the surface of the substrate. After a suitable diffusion time, the bodies are manually removed, and inoculation performed. This technique suffers from the certain disadvantage that the risk of contamination is considerable owing to the large amount of manipulation required. Furthermore, the identity readings of the reactions are made difficult and uncertain since the articles have been removed from the reaction sites before the readings take place.

The invention makes it possible by means of magnetic forces not only to deposit the bodies on the surface of the substrate, but also to remove them. This can be done, for example, by turning the substrate dish upside down and removing the bodies by means of the magnetic force generated by the magnet means in the base, the bodies being collected on paper, or other material. The identity of the reaction can be mechanically determined by their correlated positions with respect to the register marks 30, 31 which were employed as an index means for the position of the dispensing apparatus relative to the dish and base.

The articles may, in some instances, contain no active substances prior to use, and these blank articles, according to the invention, incorporate magnetically responsive material.

For testing or assaying purposes, solutions of active substances or test materials prospective of containing active substances, will be desposited by the laboratory workers into the articles, for example, paper discs.

It is possible for the active substances or test material prospective of containing active substances to be in solid form, for example, a powder. In this case liquid substrate will diffuse into the article and dissolve the solid test material resting on the top of the wettable carrier, whereafter the test material will diffuse via the carrier into the substrate.

The addition of active substances or test materials prospective of containing active substances may be made either after the articles have been positioned on the substrate, or before. In the latter case, when the additive is a liquid, the articles may be dried before they are positioned.

Positioning of the articles is carried out according to the invention, i.e. by magnetic means in order to provide a good and uniform contact with the substrate. Dispenser means comprising index means, and aligning procedures according to the invention are used in order to position the articles in predetermined spaced positions as a prerequisite to using the reader means of the invention.

The use of primarily blank articles incorporating magnetically responsive material will be very useful for an assay technique and thereby for the search for and explorartion of new active substances for the purpose of manufacturing. The procedure is applicable to improvement of manufacture and to control of products.

The use of primarily blank articles is also useful for carring out assay techniques in diagnostic laboratories, for example for the purpose of determining whether or not an active substance, for example, an antibiotic, is present in a tissue liquid, and if so for determination of its level of concentration.

It is emphasized that the method of this invention is essentially equally applicable to regular diagnostic techniques as to assay techniques. Thus, the method remains basically the same whether one is testing the activity of an agent to an active substance or whether one is testing the activity of an active substance against an agent. The difference lies solely in the object of the tests, apart from the distinction mentioned in those cases in which primarily blank articles are used instead of articles primarily containing active substances.

The reactions and the reading of the results are essentially independent of whether articles primarily containing active substances or whether blank articles to which active substances or test materials are added, are being used.

In connection with the exploration of potential vendible products and with control examinations, it should be emphasized that the invention, as in diagnostic testing, in a very high degree will improve the reliability of the tests carried out by providing more reproducible results in avoiding errors.

Additionally, the increased speed and the reduced cost of labor provided by the method of invention, makes it possible to investigate a much larger number of potential vendible products and to carry out a greatly increased number of control tests.

The value of this is especially high, because of the fact that the evaluation of the results of tests, requires a considerable number of replicate tests in the various runs of investigation in order to produce the necessary statistical significance.

For this purpose the so-called large plate method advantageously may be used, because it is very suitable for carrying out laboratory diffusion tests in accordance with an assay design. Very suitable in this connection is the use of the embodiment of magnet system and dispenser system shown in FIG. 6. Thus, the embodiment is especially useful, as in the case of large plates, when articles in large numbers are to be deposited, and the deposition points on the substrate are to be disposed in straight lines parallel to each other.

It will be understood, that in individual tests, the test components, i.e. the active substance and the agent, may prove to be inactive, in which case no reaction will occur, and the terms employed to refer to the test components should be interpreted to include this possibility.

Furthermore, the test materials may or may not contain test components, i.e. active substance or an agent. For example, one may intentionally use a well-known active substance as a test component, or one may use test materials prospective of containing active substances, such as when test materials are dropped into blank articles with a view to finding out whether or not the materials contain active substances capable of reacting with the agent present in the substrate, and if so, determination of their potencies or levels of concentration.

It is emphasized that an active substance or constituent added to an article for testing purposes, should be broadly interpreted to include both the intentional use of an active substance as well as the alternative use of a test material prospective of containing an active substance. Furthermore, it will be understood that a test material prospective of containing an active substance may be any type of test material suitable for assaying or analysis either pure or composite.

Figure 7:
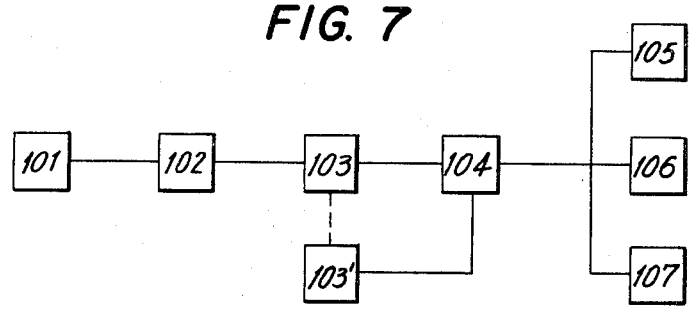
FIG. 7 is a schematic representation of a method of transmitting and storing sensitivity test data.

FIG. 7 is a schematic representation combining several features of the invention in which 101 represents the depositing or positioning of the articles containing biologically active substance on the substrate, 102 represents the incubation period, 103 represents the sensitivity reading, which for example, may be taken with a mirror reflex unit in which the results in such a case go straight to the data processing unit 104 and from there to various receivers 105, 106 and 107. When making visual readings of sensitivity, use is made of branch 103' with the results being transmitted to data processing unit 104 and from there to the various receivers 105, 106, and 107.

Another feature of this invention provides a system which achieves mechanization of primary noting (that is the direct reading and compiling of sensitivity data) for suitable bacteriological examinations and other suitable examinations, such as, for example, immunological or serological reactions taking into account the requirement for the possibility of visual and personal control and supervision. The invention contemplates a method for determining change in growth or other reaction in a solid or semi-solid substrate in connection with the primary noting of data and it is characterized in that the articles containing the substances bringing about the reaction are arranged on the surface of the substrate in a pattern of predetermined positions so that the sensitivity reactions, which can be read by a manually operated instrument having indicators arranged in oppositely disposed positions, can be checked visually while at the same time the indications may be read by machine, transmitted to a data processing unit where it can be assembled and coded, if necessary, and, thereafter, transmitted to a receiver where it can be stored for ultimate use and then subsequently read out when needed.

The identity of each reaction is determined by its position, a condition which is machine sensitive in one operation not only for one rotation but for the entire series of reactions in the pattern. It is also possible, in accordance with this invention, with the help of suitable apparatus, indicators, and the like, in a simple manner to indicate the results of the reactions on the basis of the laboratory technician's experience. These indications are also of such a nature that they are machine-sensitive and may be transmitted and stored.

The determination of the identity of the reaction and the indication of the result from visual observation may, according to the invention, by expediently combined in the same apparatus.

Figure 8:
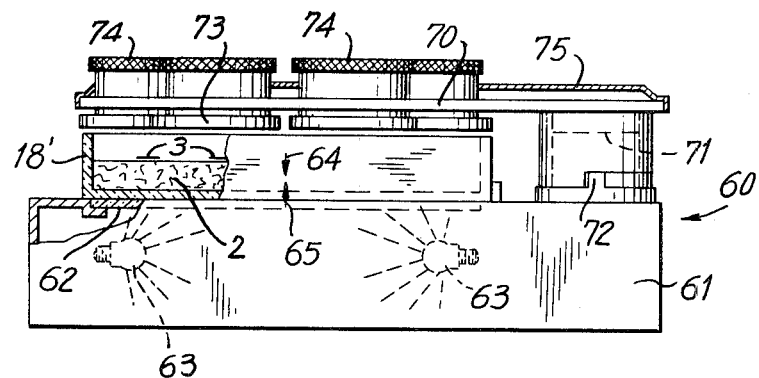
FIG. 8 is an elevational view partly in section of a reading apparatus.
Figure 9:
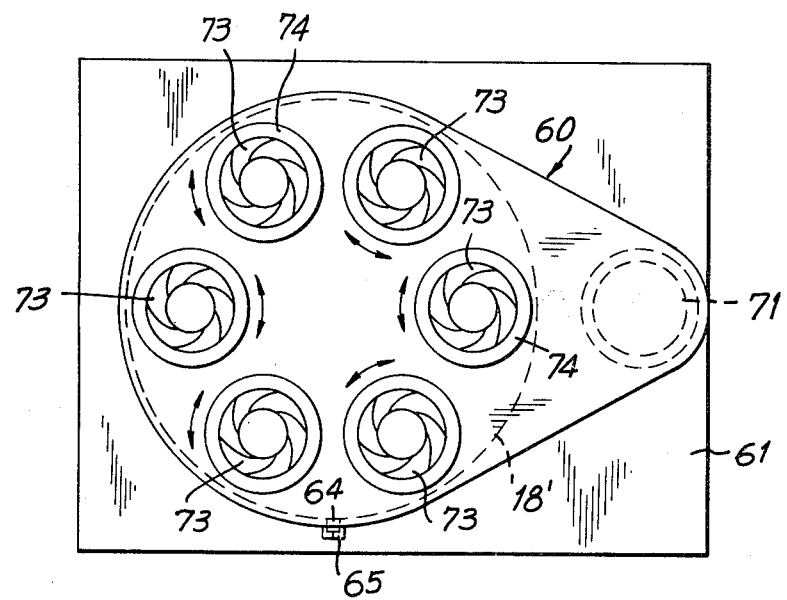
FIG. 9 is a top plan view thereof.

Referring to FIGS. 8 and 9 therein is seen petri dish 18' placed in a reading apparatus 60 for detecting the sizes of the zones of inhibition 9 surrounding the articles 3–8. The base 61 of the reading apparatus may contain electronic equipment for processing the measuring results. In the particular embodiment, it is assumed that the substrate and the bottom of the dish 18' are transparent and that the dish is centered on a glass plate 62 at the upper surface of the base 61 and illuminated from below by lig sources schematically indicated at 63. Correct angular positioning of the dish 18' on the base 61 is ensured by corresponding register marks 64 on the dish and 65 on the base. Readings are made visually through apertures in a holder 70 which is pivotably mounted in a horizontal plane about a column 71 on the base, so that it can be swung aside to facilitate insertion and removal of the dish, the operative position of which is determined by a stop 72. The position of the stop 72 is correlated with the register marks 64, 65 so that the apertures in holder 70 will be exactly above the articles 3–8. In the apertures of the holder 70 are fitted iris diaphragms 73, the aperturs of which can be adjusted by means of adjusting rings 74 which are accessible on the upper side of the cover 75. On the holder 70, under the cover, are means which sense the settings of the apertures electrically and which, via flexible leads running through the hollow supporting column, 71 are connected with electronic equipment in the base 61.

Figure 10:
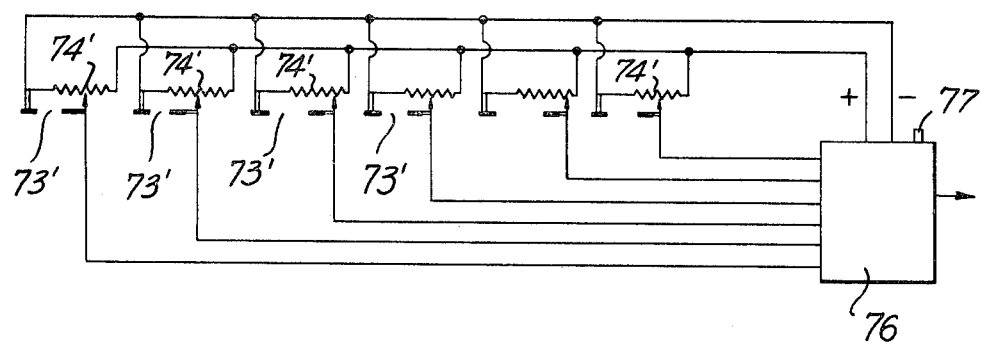
FIG. 10 is a simplified circuit diagram of a reading apparatus with a plurality of reading positions.

The means for sensing the aperture setting may be, for example, voltage dividers as shown at 74' in FIG. 10. However, for the sake of simplicity, in this figure instead of iris diaphragms 73, slot diaphragms 73'0 are shown having opposite indicator edges which can be adjusted independently of one another to opposite extremities of the respective reaction zones. One side of the indicator at all reading points is mechanically connected with the end of the voltage divider which has a negative potential, while the other side is connected to the sliding contact of the voltage divider so that the potential on each sliding contact serves as a measure of the size of the relevant aperture and thus of the measured zone diameter. With an embodiment employing iris diaphragms as in FIGS. 8 and 9 it will be possible to use a similar device with a fixed voltage-divider resistor on the holder and with sliding contacts on the adjusting rings of the diaphragms, by means of which the diaphragms are adjusted to cover the relevant zones.

The measuring voltages from the sliding contacts thus constitute analog data and are conducted via separate leads from the sliding contacts to an adapter 76. This may comprise, for example, an analog digital converter for conversion of the and data to a binary code and may be programmed to coordinate individual measuring data with data relating to the relevant active substances, these being identified by the individual leads for the respective positions. From the adapter, the data so coordinated can be delivered for registration either directly in a computer or on a punched tape or similar medium, which each time is first provided with identification data and then with measuring data. Relaying from unit 76 can be done either in turn as and when measurements are made, or at the end, after all the indicators have been adjusted, as the leads from the sliding contacts can be connected to contacts in a multiplexer which is released by pressing a button 77.

Should there be more reading positions than occupied positions, the sliding contacts in the unoccupied positions will be in the zero position; this will have no effect on the remaining readings. And if by chance a position should be missed in the reading process, the only consequence will be that the measurementin question will be lost, as all the measurements made will remain alloted to their respective, correct identifications.

Although in FIG. 8 the articles containing the active substance are deposited on the substrate during measurement it makes no difference if the articles have been removed from the substrate before measurements are made, as for example in prediffusion techniques, as measurement is only undertaken on the formed zones. It will be recalled that in prediffusion techniques, inoculation of the substrate is performed after the articles have been in contact with the substrate for a certain period in which diffusion takes place and subsequently the articles are removed.

Figure 11:
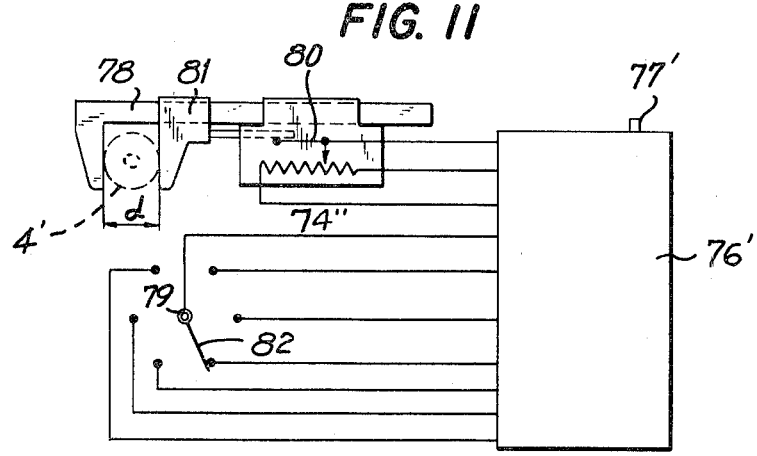
FIG. 11 is a similar view of a reading apparatus in which each reaction zone is measured in succession with the same measuring device.

FIG. 11 shows a simpler embodiment of reader apparatus, employing only one measuring instrument, in the form of a sliding gauge 78 similar to a micrometer. The substrate is illuminated by a light falling onto it so that under normal circumstances it will not be necessary to provide illumination from below through the bottom of the dish. The dish is mounted on a base or turntable supported on a rotatable shaft 79. The indicators of the gauge 78 are adjusted to the diameter of the reaction zone, which is indicated by a broken line at 4'. The gauge supports a voltage divider 74" fitted with a sliding contact 80 mechanically connected to a movable indicator 81 of the gauge. The voltage on the sliding contact thus again constitutes a measure of the measured zone diameter d and is relayed to an adapter 76'. Voltage is also applied to a selector arm 82 which is insulated and mounted on the shaft 79 and in turn cooperates with fixed contacts placed at angular distances corresponding to the various positions in the dish when this is properly aligned at an index or measuring position. The fixed selector contacts are connected in turn via separate leads with the adapter 76'. The measuring instrument 78 is employed at the same location and the dish is rotated on a turntable to bring the measuring zones to the instrument. The instrument can be supported on a suitable radial guide. Alternatively, the instrument may be connected with the unit 76' by flexible connectors so as to be portable. The axle 79 of the turntable is turned to turn the dish, after each reading, through an angle corresponding to the angular spacing between the measuring zones. In this case the registration are performed successively, in other words, for example, by the set position and the set voltage being registered coordinately for each individual reading by pressing a button 77'.

Instead of using voltage dividers which cooperate with an analog digital converter in the adapter, it is, of course, also possible to use other components for the purpose, e.g. to fit binary position encoders with direct mechanical connection to the measuring instruments.

Finally, it is possible to use the apparatus as shown in the drawing not only to measure diameters, but also to supply data for indicating the absence or presence of a reaction or for grading positive reactions, by assigning to such observations specific settings of the measuring instruments. This is applicable not only for diffusion testing but also for testing not involving diffusion such as, phage typing. In fact, it is applicable to various biochemical and chemical tests, such as clinical chemical test; so-called spot tests;and immunofluorescent techniques. Such biochemical tests may include, for example, color change in the article itself, e.g. in a test for urease production by microorganisms.

The identification of the reaction and indication of its result may be fed into a central data unit as two machine sensitive functions. In this manner, it has been possible to establish a primary noting by machine of bacteriological or other data in machine contact with a central data processing unit with the excellent advantages offered. Such advantges, are, for example, saving in recording, storing, communication and analysis of the data.

In the first phase of data processing, the primary noting handles the basic material on which the subsequent phases of the process build. By mechanical means primary noting is much more reliable than manual means, and faster registration and flow is thus possible. During manual primary noting of data, errors may easily arise, not the least of which occurs in bacteriological and similar examinations (for instance, serological examinations) in which the reading or collecting of data can be monotonous. The reactions which are uniform and usually occur in large numbers are as a rule, only differentiated under the guidance of memory. As identifying marks, various colors or symbols on the tablets or other articles containing biologically active substances which occur in the reactions are used, or the marks may be indicated by typical laboratory markers (such as, for example, a grease pencil) on the bottom of the petri dish. When at the same time measurements have been made and noted manually, the possibility of error arises.

Errors such as these in primary noting are very difficult to discover and correct. In consequence, errors are introduced in the basic material with all the complications which are later involved in further processing. Results may be interchanged, and the faulty data is compiled concerning what has been found in the patients. This, in turn, could lead to incorrect treatment. Incorrect measurements or notation can also result in many other complications. Thus, errors in primary notation can lead to complications in the detection of infectious diseases and the large group of epidemics caused by microbes. It is evident that by the use of the system in accordance with this invention errors of this nature are kept to a minimum and a high degree of reliability can be placed on the data collected and stored through the electronic data processing unit.

A central health registry system can be established in accordance with this invention. The objective is to build up an intergrated communication system between various sectors of community health services. By way of example, it shall be possible when admitting a patient to the hospital to speedily and reliably collect information from a central storage unit with respect to any earlier stays in the hospital or other examinations which may have been made. New findings of possible interest may similarly be at the disposal of the attending physician. It must be possible to provide cumulative transcriptions concerning findings for patients. A correct basic material plays here, as elsewhere, a decisive role, the effect of which the invention will be able to realize with regard to the examinations made. Similarly the effect of the information on the realization of a speedy flow will be of vital significance, particularly in acute and dangerous cases.

In the bacteriological laboratory, it is, generally speaking, unusual to carry out the work with a system in mind whereby a growth or a reaction is to be placed in a position or in a pattern. Normally, the inoculation of the material of the placing of the reactions occurs at random on the surface of a substrate or in a tube containing a liquid substrate.

Viewed as a whole, the method of this invention for collecting, transmitting and storing laboratory information proceeds in distinct phases or steps.

In the first phase the agent is inoculated on or in the substrate, and as a rule the positioning of articles is carried out the effects or reactions of which is to be tested. Such articles may include antibiotics whose sensitivity to microbes is to be determined.

In the second phase incubation is carried out in order to develop the growth and/or other reaction. The container in which the inoculated substrate lies is placed in an incubator usually at about 37° C. It usually remains there 18 to 24 hours. Sometimes the period may be shorter, but it may also extend up to several weeks.

The conditions should desirably and substantially be under control. If, in a particular technique there is required a secondary application, as, for example, of an article containing another substance, this should desirably be done also under control conditions, such as, control of time at which it is applied, control of amount added and of the site at which the addition takes place.

In the third phase the results are read and their nature and extent recorded.

Very wide-spread is, for example, the usage of antibiotics in the form of small, at least approximately, circular tablets paper discs, and similar bodies containing the antibiotics. These are, in accordance with this invention, guided by means of the magnetic attraction into the desired position on the surface of an inoculated substrate in good contact with the substrate. After an incubation period the effects are automatically read off under the control of the operator by measuring the spread of area of sensitivity which is formed around the individual antibiotic bodies.

In contrasdistinction, the prior art requires manual procedures which are exacting and demanding, and above all, time consuming. This is becoming a serious problem due to the increasing numbers of such tests in laboratories. Such manual procedures as positioning the individual bodies requires skill and is laborious while additionally, manual reading is cumbersome and time consuming and must be carefully made in order to obviate erroneous readings which could have fatal consequences as the treatment of the patient concerned is decided, on the basis of such sensitivity determinations.

In accordance with the invention, this is avoided by automatically locating the bodies containing the antiobiotics at specific predetermined locations and correlating the reading or measurement of the reaction zones at said predetermined locations whereby for each reading, two signals are always produced, one for the magnitude of the reading, the other for the identificaton thereof.

In order to insure that the location of the reaction region will conform exactly with the reading position it is necessary to correlate the deposit of the articles with the position of the reader. In order to achieve this the invention contemplates a simplified means for establishing releasable coupling between the support or container for the substrate and the respective dispenser and reader.

Referring to FIGS. 12-15 therein are shown various constructions of orientation and releasable coupling means for proper orientation and support of a dispenser device and a reader device on the container for the substrate.

Figure 12:
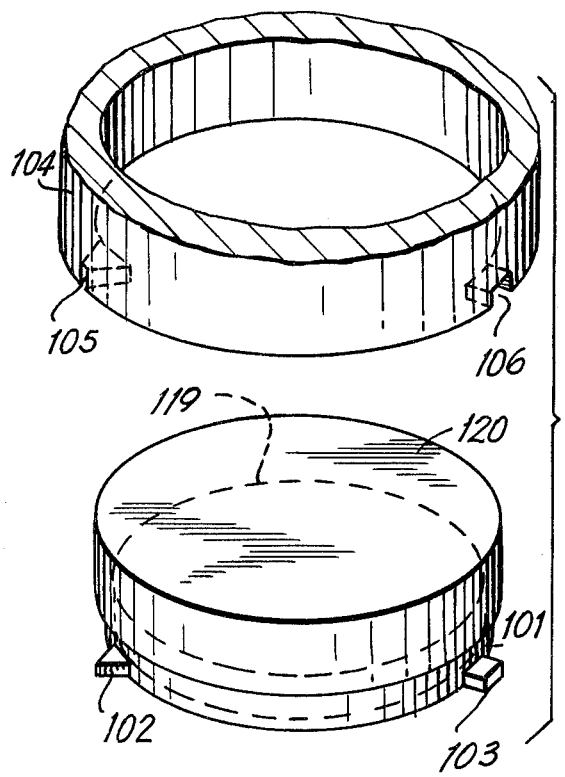
FIG. 12 is a perspective view of a container with a cover thereon.

Thus referring to FIG. 12, therein is seen a container 101 with a substrate 119 therein. At the bottom of the outer periphery of the container 101, there are placed two protuberances 102, 103 in angularly offset relation. Protuberance 102 is triangular and protuberance 103 is rectangular. The reader device and the dispenser device are each provided with a casing 104 having notches 105 and 106 of a shape corresponding to the protuberances 102 and 103 such that when engaged therewith the casing 104 is angularly oriented and locked with the container 101. Thereby, the position of the dispenser device and reader device will be fixed with respect to the container and the accuracy of reading of the dispensed articles on the container will be insured.

Figure 13A:
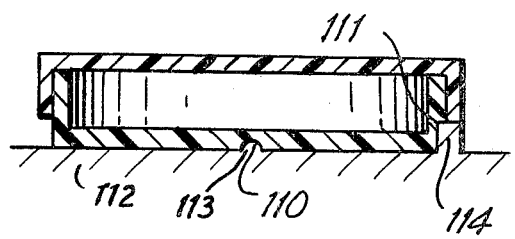
FIG. 13a is an elevation view of a modified container with the cover thereon.
Figure 13B:
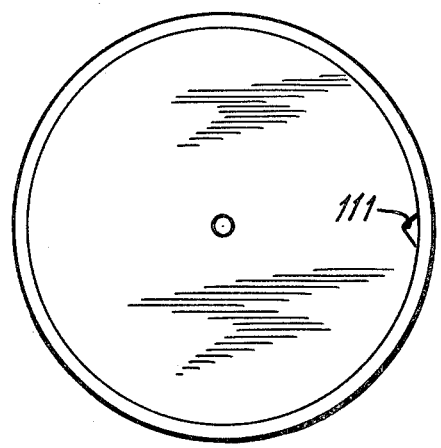
FIG. 13b is a plan view of the container of FIG. 13a with the cover removed.

FIGS. 13a and 13b show a modified arrangement and herein the bottom of the container 101 is provided with a central recess 110 and the periphery is provided with a triangular groove 111. The dispenser and reader are formed with base 112 having an upstanding pin 113 which fits into the recess 110 and an upstanding post 114 of triangular shape for fitting into groove 111.

Figure 14:
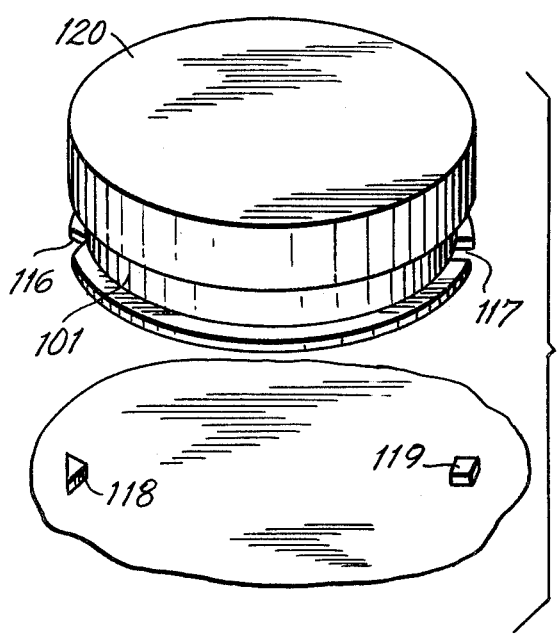
FIG. 14 is a perspective view showing a modified embodiment of the container with the cover thereon.
Figure 15:
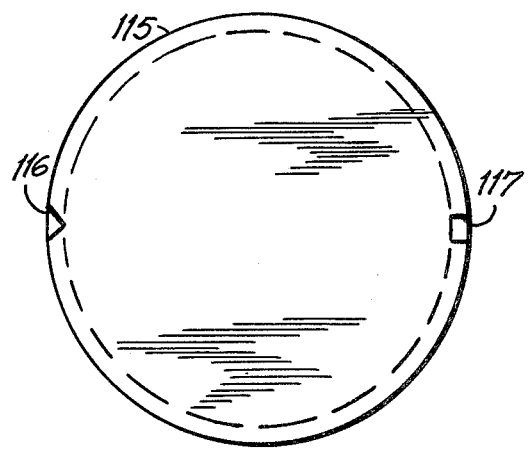
FIG. 15 is a plan view of the container of FIG. 14 with the cover removed.

FIG. 14 shows a modified arrangement in which the container 101 is formed with an annular flange 115 having two slots 116 and 117 threin of different shape, slot 116 being triangular and slot 117 being rectangular. These slots accommodate posts 118 and 119 formed on a base of a respective dispenser device and reader device.

In FIG. 12 and 14, the container 101 is shown with a cover 120 thereon. The flange 115 in the embodiment of FIG. 14 extends radially outwardly a distance equal to the rim of the cover 120.

It will be understood that the recesses and corresponding projections can be formed on the respective elements in any suitable fashion. Additionally, it is to be understood that the cooperation of the container can be made in the same maner as described above with the magnetic base.

Although the present invention has been described in conjunction with preferred embodiments, it is to be understood that various modifications and variations thereof will become apparent to those skilled in the art without departing from the spirit and scope of the invention as defined in the appended

What is claimed is:

1. Apparatus for testing reactions comprising a support for a substrate capable of containing an agent, dispenser means for guiding and depositing a plurality of individual articles adapted for containing respective active constituents onto said substrate in spaced relation at pre-determined location, means for bringing said articles into contact with the substrate at a pre-determined operative contact pressure, said constituents undergoing respective reaction with the agent of said substrate and producing detactable results, reader means for determining said detectable results at said predetermined locations, and means for releasably coupling and orienting the support respectively with the dispenser means to predetermine the locations of said articles on the substrate and with the reader means so that the position at which the reader means determines the said detectable results is also determined.

2. Apparatus as claimed in claim 1 wherein said reader means includes means for detecting the presence or absence of a reaction and for grading reactions when they are present.

3. Apparatus as claimed in claim 1 comprising magnetically responsive means operatively coupled to said articles, and means on said support for producing a magnetic field for acting on said magnetically responsive means to urge the articles against said substrate.

4. Apparatus as claimed in clain 1 wherein said reader means comprises a plurality of reader devices for determining said detectable results at respective of said predetermined locations.

5. Apparatus as claimed in claim 1, wherein said detectable result is variation in the size of a zone surrounding each article, said reader means comprising adjustable aperture means for measuring the size of said zones.

6. Apparatus as claimed in claim 1 wherein said articles each comprises magnetically responsive means incorporated therewith, said apparatus further comprising means on said support means to produce a magnetic field and urge the articles against said substrate.

7. Apparatus as claimed in claim 1 comprising data processing means for receiving electrical signals from said reader means.

8. Apparatus as claimed in claim 1 wherein said articles are discs and said dispenser means includes means for supporting a stack of discs.

9. Apparatus as claimed in claim 4 wherein each said reader device includes a respective measuring device.

10. Apparatus as claimed in claim 1 wherein said reader means consists of a single reader device.

11. Apparatus for testing reactions comprising support means for a substrate capable of containing an agent, dispenser means for depositing a plurality of articles adapted for containing respective active constituents onto said substrate in said support means in spaced relation, the reactivity of said constituents with the agent of said substrate being determined by the production of detectable results, index means for orienting the dispenser means and said support means relative to one another, reader means correlated with said index means for determining said detectable results, said index means including means for releasably coupling and orienting the support means respectively with the dispenser means to pre-determine the locations of said articles on the substrate and with the reader means so that the position at which the reader means determines said detectable results is at the pre-determined locations of the aticles, said reader means including a first means for producing a first electrical signal for each article for indicating the magnitude of the result, a second means for producing a second electrical signal indicative of the identity of the article being examined and a third means for correlating said first and second signals for each particular article.

12. Apparatus as claimed in claim 10 wherein said reader device consists of a single measuring device.

* * * * *